United States Patent
Kumaraswamy et al.

(10) Patent No.: US 10,722,462 B2
(45) Date of Patent: Jul. 28, 2020

(54) DISCONTINUOUS REVERSE MICELLAR COMPOSITION IN CUBIC FD3M PHASE FOR SUSTAINED RELEASE OF THERAPEUTIC DRUGS

(71) Applicant: Council of Scvientific and Industrial Research, New Delhi (IN)

(72) Inventors: Guruswamy Kumaraswamy, Pune (IN); Manoj Kumar, Pune (IN); Ashootosh Vasant Ambade, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 33 days.

(21) Appl. No.: 15/534,616

(22) PCT Filed: Dec. 10, 2015

(86) PCT No.: PCT/IN2015/050196
§ 371 (c)(1),
(2) Date: Jun. 9, 2017

(87) PCT Pub. No.: WO2016/092569
PCT Pub. Date: Jun. 16, 2016

(65) Prior Publication Data
US 2017/0319481 A1   Nov. 9, 2017

(30) Foreign Application Priority Data

Dec. 10, 2014   (IN) .................... 3631/DEL/2014

(51) Int. Cl.
*A61K 9/107* (2006.01)
*A61K 9/14* (2006.01)
*A61K 47/14* (2017.01)
*A61K 31/192* (2006.01)

(52) U.S. Cl.
CPC .......... *A61K 9/107* (2013.01); *A61K 9/146* (2013.01); *A61K 31/192* (2013.01); *A61K 47/14* (2013.01)

(58) Field of Classification Search
None
See application file for complete search history.

(56) References Cited

U.S. PATENT DOCUMENTS

| | | | |
|---|---|---|---|
| 2003/0022242 A1* | 1/2003 | Anderson | A61K 9/1274 435/7.1 |
| 2003/0027784 A1* | 2/2003 | Kissel | A61K 48/00 514/44 R |
| 2005/0064027 A1* | 3/2005 | Jacob | A61K 9/0065 424/451 |
| 2007/0213234 A1 | 9/2007 | Yaghmur et al. | |
| 2010/0087535 A1* | 4/2010 | Tsunenaga | A61K 8/44 514/563 |
| 2014/0186279 A1* | 7/2014 | Joabsson | A61K 9/0014 424/59 |
| 2014/0348903 A1 | 11/2014 | Tiberg et al. | |

FOREIGN PATENT DOCUMENTS

| | | | |
|---|---|---|---|
| EP | 0126751 | 5/1988 | |
| EP | 2604253 | 6/2013 | |
| WO | 2013030838 | 3/2013 | |
| WO | WO-2013087791 A1 * | 6/2013 | ............. A61K 8/375 |

OTHER PUBLICATIONS

Fleischer, M. et al., "Transforming polyethylenimine into a pH-switachable hydrogel by additional supramolecular interactions," Chem. Commun., published Jul. 23, 2014, 50, pp. 10464-10467.*
N. Sahiner et al., "PEI-based hydrogels with different morphology and sizes: Bulkgel, microgel, and cryogel for catalytic energy and environmental catalytic applications," European Polymer Journal 76 (2016) 156-159.*
Rappolt, M. et al. "How the Chain Configuration Governs the Packing of Inverted Micelles in the Cubic Fd3m-phase", Soft Matter, vol. 9, No. 27, Jan. 1, 2013, p. 6291, XP055260767, GB.

* cited by examiner

*Primary Examiner* — Monica A Shin
(74) *Attorney, Agent, or Firm* — Carmody Torrance Sandak & Hennessey LLP (57) ABSTRACT

The present invention discloses reverse/inverse micellar discontinuous cubic phase (Fd3m phase) composition for controlled release of therapeutic drugs or biologically active component and to the process for preparation thereof.

8 Claims, 7 Drawing Sheets

DISCONTINUOUS REVERSE MICELLAR COMPOSITION IN CUBIC FD3M PHASE FOR SUSTAINED RELEASE OF THERAPEUTIC DRUGS

FIELD OF THE INVENTION

The present invention relates to a discontinuous reverse micellar composition in cubic fd3m phase for sustained release of therapeutic drugs or biologically active component and to the process of preparation thereof. More particularly the present invention relates to the process for preparation of stable, discontinuous reverse micellar composition stacked in to Fd3m phase.

BACKGROUND OF THE INVENTION

Surfactants, lipids, and polymer molecules that have both polar and nonpolar components are termed as amphiphilic molecules. The hydrophobic effect drives the amphiphilic molecules in polar solvents to spontaneously self-assemble into a rich array of thermodynamically stable lyotropic liquid crystalline phases. The liquid crystalline phases possess a sufficient average degree of molecular orientational order, characterized by their structural symmetry, and are often formed in aqueous surfactant systems at relatively high amphiphile concentration.

The molecular structures of lipids play an important role in the determination of phase behavior. The critical packing parameter (P) is used to predict the nanostructure of formed liquid crystal with the formula $P=v/a\,l$, where P is critical packing parameter, 'v' is the hydrophobic chain volume, 'a' is the cross-sectional area of the polar headgroup, and 'l' is the hydrophobic chain length.

When, $P<1$, oil-in-water self-assembled structures are formed, such as normal micelles ($L_1$), normal cubic structure ($V_1$), and normal hexagonal phases ($H_1$). When $P>1$, water-in-oil self-assembled structures are formed, such as reversed micelles ($L_2$), reversed cubic structure ($V_2$), and reversed hexagonal structure ($H_2$).

There are several different types of lyotropic liquid crystal structures where each of these different types has a different extent of molecular ordering within the solvent matrix. One such example is the bicontinuous cubic liquid crystalline phase.

Lipids, such as glycerol monooleate form mesophase structures that are thermodynamically stable, such as the bicontinuous phases with Ia3d and Pn3m symmetry. Phases such as the Pn3m are stable in the presence of excess water. Therefore, they are amenable to formulation as particle dispersions. These phases can be loaded with drugs that can be subsequently released. The fact that these are thermodynamically stable makes them especially suitable for pharmaceutical formulations.

One main problem with these phases, especially for the particle dispersions is that they give a burst release of loaded drugs. Therefore, control of the release rate is currently difficult and is of significant importance to pharmaceutical applications.

It is therefore important to provide composition and the processes for stabilizing fluid amphiphile interfaces. Since the advent of the first patent in 1984 [EP0126751] when the highly ordered cubic phase was proposed as an interesting matrix in controlled release preparations, lipid-based liquid crystal systems have been extensively investigated in drug delivery, as well as the potential application in theranostic nanomedicines. These prior art have mainly taught the use of bicontinuous micellar phases for applications in drug delivery and theranostics. However, rapid release of hydrophilic drugs from such bicontinuous phases limits their applications. Therefore, controlled decrease of the release rate of encapsulated drugs is of great importance.

This is made possible by forming inverse discontinuous micellar phases such as the Fd3m symmetry phase.

Discontinuous cubic phases are intermediate liquid crystalline phases and reside between hexagonal phases and micelles. Discontinuity is attributed to discretely ordered aggregates of micellar structures and hence either the water or hydrocarbon phase is discontinuous.

Article titled 'Oil-Loaded Monolinolein-Based Particles with Confined Inverse Discontinuous Cubic Structure (Fd3m)' by Anan Yaghmur et.al published in Langmuir, 2006, 22 (2), pp 517-521 reports discontinuous micellar cubic phase of the symmetry Fd3m consisting of MLO (monolinolein)—water—TC (tetradecane) system at a specific TC/MLO weight ratio with TC-loaded aqueous dispersions in the confined intermediate phase i.e Fd3m phase. The article discloses the use of ahydrophobic additive, tetradecaneoil to modulate the texture of liquid crystals which result in phase transition.

Further, an interesting property of the cubic phases formed by certain classes of amphiphiles is their ability to be dispersed into particles, termed cubosomes. Cubosomes are liquid crystalline nanostructured particles with the same unique properties of the bulk cubic phase, although cubosome dispersions have much lower viscosity.

Cubic phases are used to improve the drug bioavailability and reduce drug toxicity. Yang et al. [Z. Yang, Y. Tan, M. Chen et al., "Development of amphotericin B-loaded cubosomes through the SolEmuls technology for enhancing the oral bioavailability," AAPS PharmSciTech, vol. 13, no. 4, pp. 1483-1491, 2013.74] prepared PT-based cubosomes containing amphotericin B (AmB) to improve its bioavailability and reduce nephrotoxicity. Esposito et al. [E. Esposito, R. Cortesi, M. Drechsler et al., "Cubosome dispersions as delivery systems for percutaneous administration of indomethacin," Pharmaceutical Research, vol. 22, no. 12, pp. 2163-2173, 200596] studied the performance of cubosomes as sustained percutaneous delivery systems with the model drug molecule of indomethacin.

The present inventors observed that formation of Fd3m phases, however, requires the addition of significant quantities of nonpolar materials (such as oils) making the process of formulation more difficult.

With a view to design adequate mesophase delivery system for sustained release of the drug, the present invention provides a composition using lipid and small quantities of hydrophilic polymer with a well-defined size and compact shapecapable of inducing sufficient curvature in the lipid assembly to form an Fd3m phase effortlessly.

The use of hydrophilic polymers in formation of reverse micellar phases is disclosed in US2005079145, WO2013030838 or KR20090027809, however, said applications fail to disclose the use of hydrophilic polymers in lipid/water system to induce Fd3m phase for sustained release of the therapeutic drugs or biologically active component.

OBJECTIVE OF THE INVENTION

Main object of the present invention is to provide a composition comprising lipid and small quantities of compact, macromolecular polymers which induces the formation of Fd3m phase, effective for controlled/sustained release of pharmaceutical compound.

The other object of the invention is to provide a process for preparation of said novel composition using small quantity of hydrophilic polymer and by avoiding use of large quantity of non-polar oils to the lipid/water mixture.

Yet another object of the invention is to provide a pharmaceutical composition which induces Fd3m phase suitable for controlled release of the drug or biologically active component.

SUMMARY OF THE INVENTION

Accordingly the present invention provides a stable, discontinuous reverse micellar composition stacked in a cubic Fd3m phase comprising:
  i. a moiety 'A' selected from water soluble branched polymer with molecular weight in the range of 0.5-5 kDa or polar interacting particles of size less than 5 nm or molecular cages of size less than 5 nm;
  ii. moiety '13' lipids and
  iii. moiety 'C' a hydrophilic phase;
  wherein weight fraction of moiety 'C' relative to moiety 'B' is in the range of 10-40 wt %; moiety 'A' is in the ratio 0.5-10 wt % relative to moiety 'B' and moiety 'C'.

In an embodiment of the present invention, the water soluble branched polymer is selected from polyethyleneimine (PEI) or dendrons of polyamidoamine (PAMAM) preferably PEI.

In another embodiment of the present invention, dendrons of polyamidoamine (PAMAM) is selected from the group consisting of PAMAM G2 amine with 4-$NH_2$ groups, PAMAM G3 amine with 8-$NH_2$ groups, PAMAM G4 amine (with 32-$NH_2$ groups preferably PAMAM G4 amine with 32-$NH_2$ groups.

In yet another embodiment of the present invention, polar interacting molecular cages used is Polysilsesquioxane hydrate-octakistetramethylammonium substituted (POSS).

In still another embodiment of the present invention, lipids used are selected from polar or non-polar surfactant and the non-polar surfactant is selected from the group consisting of Glyceryl monooleate (GMO, 2,3-dihydroxypropyloleate), phytantriol (PT, 3,7,11,15-tetramethyl-1,2,3-hexadecanetriol), monolinolein, monoelaidin, phosphatidylethanolamine, oleoylethanolamide, phospholipids, PEGylated phospholipids, alkyl glycerates, and glycolipids either alone or combination thereof.

In yet another embodiment of the present invention, the hydrophilic phase used is water.

In yet another embodiment, present invention provides a process for preparation of stable, discontinuous reverse micellar composition stacked in to Fd3m phase comprising the steps of:
  i. mixing 0.5-10 wt % water soluble polar branched polymer of molecular weight 0.5-5 kDa or polar interacting particles of size less than 5 nm or molecular cages of size less than 5 nm to a solution of lipid and water followed by addition of 30% (v/v) $HNO_3$ to adjust the pH of the polymer in solution to pH 10; and
  ii. heating the mixture as obtained in step (i) at a temperature in the range of 60-80° C. and allowing the mixture to equilibrate for a period of 10-15 days to obtain stable, discontinuous reverse micellar composition stacked in to Fd3m phase.

In yet another embodiment, present invention provides a pharmaceutical composition comprising of micellar composition and an active selected from pharmaceutical drug or biologically active component.

In yet another embodiment of the present invention, the pharmaceutical drug or biologically active component is selected from Naproxen sodium, aspirin, vitamin E, propantheline bromide, oxybutynin hydrochloride, metronidazole, tetracycline, timolol maleate, chlorpheniramine maleate, propranolol hydrochloride, melatonin, pindolol, propranolol and pyrimethamine, hemoglobin, cefazolin, insulin, capsaicin, cinnarizine, diclofenac salts, and such like.

In yet another embodiment, present invention provides a composition useful in sustained release of an active selected from pharmaceutical drug or biologically active component.

In yet another embodiment, present invention provides a method for sustained release of an active selected from pharmaceutical drug or biologically active component comprising administering to a subject in need thereof an effective amount of pharmaceutical composition comprising discontinuous reverse micelles stacked in a cubic Fd3m phase and an active.

ABBREVIATIONS USED

GMO: Glycerol monooleate
PAMAM: Polyamidoamine

BRIEF DESCRIPTION OF FIGURES

FIG. 3 depicts influence of (2%, 4% and 6%) Dendron G4 i.e PAMAM on (a) GMO:water (80%:20%) system at RT; (b) on GMO:water (85%:15%) system at RT; (c) on GMO: water (75%:25%) at RT

FIG. 5 depicts SAXS data for GMO/water: (a) and (a*) 80/20 w/w; (b) 85/15 w/w; (c) 75/25 w/w containing G3 PAMAM dendron and L3 (linear analog). The systems represent (a) 80/20/ØG3; (a*) 80/20/ØL3 (b) 85/15/ØG3 and (c) 75/25/ØG3, where Ø represents the additive concentrations.

DETAILED DESCRIPTION OF THE INVENTION

The present invention provides a reverse micellar composition that can tune the curvature of lipid/water assemblies critically dependent on the chain architecture of the ternary polar macromolecular polymer inclusion. The inclusion of polar, water soluble polymer does not mitigate packing frustration. On the contrary, strong interactions between the amine groups and the lipid head groups compensate for the increase in free energy due to the increased curvature of the discontinuous micellar phases, inducing Fd3m phase formation.

Addition of compact, polar macromolecular additives to lipid/water assemblies results in conversion of bicontinuous reverse micelle to discontinuous Fd3m phase. The additives influence the mesophase behavior consequently resulting in providing sustained/controlled release of pharmaceutical drug or biologically active component.

In accordance with the above, the present invention discloses a stable, discontinuous reverse micellar composition stacked in a cubic Fd3m phase for sustained release, comprising;

a moiety 'A' selected from water soluble branched polymer with MW in the range of 0.5 to 5 kDa or polar interacting particles of size less than 5 nm or molecular cages of size less than 5 nm;
moiety 'B' selected from lipids;
moiety 'C' hydrophilic phase;
wherein weight fraction of moiety 'C' relative to moiety 'B' is in the range of 10-40 wt %;
moiety 'A' is in the ratio 0.5-10 wt % relative to moiety 'B' and moiety 'C'.

In a preferred aspect, addition of 2-4 wt % of water soluble branched polymer in the lipid/water system induces Fd3m phase.

The moiety 'A' is selected from water soluble branched polymer with MW in the range of 0.5-5 kDa comprising acrylics such as acrylic acid, acrylamide, and maleic anhydride polymers and copolymers; amine-functional polymers including allylamine, ethyleneimine, oxazoline, and other polymers containing amine groups in their main- or side-chain such as polyethyleneimine (PEI), hydroxyalkylacrylate, a hydroxyalkylmethacrylate, a polyhydroxyalkylacrylate, polyhydroxymethacrylate; polyamidoamine; Poly (amino ethyl meth acrylamide and such like.

The particles of size less than 5 nm or molecular cages of size less than 5 nm are selected from Polysilsesquioxane hydrate-octakistetramethylammonium substituted (POSS). The nanoparticles (<5 nm) are water dispersible (polar) and interact strongly with the GMO headgroup.

The moiety 'A' is selected from branched polymer that bears primary, secondary and tertiary amine groups such as polyethyleneimine (PEI), dendrons that display terminal amine groups selected from polyamidoamine (PAMAM) such as PAMAM G2 amine (with 4-NH2 groups); PAMAM G3 amine (with 8-NH2 groups); PAMAM G4 amine (with 32-NH2 groups).

The moiety 'B' is selected from ionic or non-ionic surfactants, preferably non-ionic surfactants comprising Glyceryl monooleate (GMO, 2,3-dihydroxypropyloleate), phytantriol (PT, 3,7,11,15-tetramethyl-1,2,3-hexadecanetriol), monolinolein, monoelaidin, phosphatidylethanolamine, oleoylethanolamide, phospholipids, PEGylated phospholipids, alkyl glycerates, and glycolipids either alone or combination thereof; preferably the non-ionic surfactant is Glyceryl monooleate (GMO, 2,3-dihydroxypropyloleate).

The moiety 'C' hydrophilic phase in the composition is water.

The pH of the ternary mixture comprising GMO/water/Polymer is maintained at pH 10 due to the following reasons; (a) the amine polymer has a very low degree of protonation at said pH; and (b) the GMO does not undergo hydrolytic degradation.

The temperature of the ternary system is maintained in the range of 25–80° C.

The present invention discloses stable, discontinuous reverse micellar composition stacked in a Fd3m phase comprising polyethyleneimine (PEI) with molecular weight in the range of 1 to 2 kDa; Glycerol monooleate (GMO) and water, wherein the weight fraction of PEI relative to GMO and water is in the range 2-4%; the weight fraction of water relative to GMO is in the range 10-40%.

The effect of polymer (PEI) concentration to the GMO/water system was evaluated at varying concentrations of PEI. Accordingly, on addition of PEI, the GMO/water sample showed a marked change in appearance and viscosity. In the 90/10% (w/w) GMO/water system which is a low viscosity clear phase in the neat system, addition of 2 wt. % PEI (relative to the GMO/water system) transformed it to a transparent high viscosity gel phase. Further increase in PEI content (≥4 wt. %) resulted in the development of opacity. Similar behavior was observed in the 85/15% (w/w) (GMO/water) system where samples gelled and turned opaque at ≥2 wt % PEI (relative to GMO/water). For the GMO/water systems (80/20, 75/25, 70/30, 65/35 and 60/40% w/w) the samples turned opaque for PEI >2 wt %.

The phases formed were determined with the help of SAXS. A lamellar phase with 0% PEI (GMO/water: 90/10 & 85/15 w/w) showed a transition into Ia3d phase with 0.3% PEI. For 0.5 wt % PEI, the lamellar phase transformed into the inverse hexagonal phase (H2). When the PEI content exceeded 3% the GMO/water (90/10) system transformed into the opaque Fd3m phase. Similar behavior was observed with the PEI in the 85/15 (GMO/water) system where the Fd3m phase was formed for ≥2 wt. % PEI.

The effect of temperature on GMO/water system of varying concentration ratio i.e. 90/10, 85/15, 80/20, 75/25, 70/30, 65/25, and 60/40 wt. %) with PEI content=0.5, 1, 2 wt. % was conducted. The temperature was varied from ambient to 92° C. Similarly, the temperature change for the higher molecular weight systems (25 kDa and 70 kDa) was also performed. Fd3m phase was obtained only for a certain range of branched PEI molecular weight (~1-2 kDa) and not for higher molecular weight (25 and 70 kDa).

The addition of 2-4 wt % of PEI to the GMO/water system, with the 10-40 wt % of water relative to GMO induced Fd3m phase.

The PEI molecules are localized within micellar GMO structures which are responsible for Fd3m phase. The equilibrium structure formed when PEI is incorporated in GMO/water was observed to be governed by several factors. Firstly, PEI interacts with GMO and dehydrates the head group size resulting in a change in the effective head group size. The conformational entropy of the PEI is reduced when it is incorporated within the organized lipid structure. This change in conformational entropy is a function of polymer architecture: chain molecular weight and branched structure. The present inventors observed that the combination of all these factors resulted in an enhanced stability for the Fd3m phase for a PEI molecular weight of 2 kDa.

The present invention discloses GMO/water/2 kDa PEI system that forms stable, discontinuous reverse micellar Fd3m phase with weight fraction (fw) of water in the range 10-40 wt % and polymer weight fraction of 2%. From the SAXS data, the lattice parameter associated with the Fd3m phase was calculated at 157 Å. The Fd3m phase comprises reverse micelles arranged in an AB2 crystal structure with Fd3m symmetry.

The present invention discloses stable, discontinuous reverse micellar composition stacked in a Fd3m phase comprising dendron selected from polyamidoamine (PAMAM) with molecular weight in the range of 0.5 to 5 kDa;

Glycerol monooleate (GMO) and water, wherein the weight fraction of PAMAM relative to GMO and water is in the range 2-6% and weight fraction of water relative to GMO is in the range 10-40%.

The Dendron is selected from polyamidoamine (PAMAM) such as PAMAM G2 amine (with 4-NH2 groups); PAMAM G3 amine (with 8-NH2 groups); PAMAM G4 amine (with 32-NH2 groups). The PAMAM dendrons with peripheral amines (G2 to G4) of the present invention were synthesized by a known procedure [ref: Lee, J. W.; Kim, J. H.; Kim, H. J.; Han, S. C.; Kim, J. H.; Shin, W. S.; Jin, S.-H. Bioconjugate Chem. 2007, 18, 579].

Figure 3A:
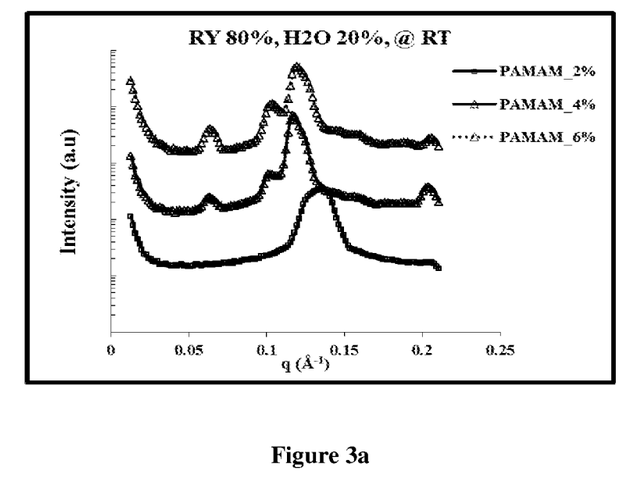
Figure 3B:
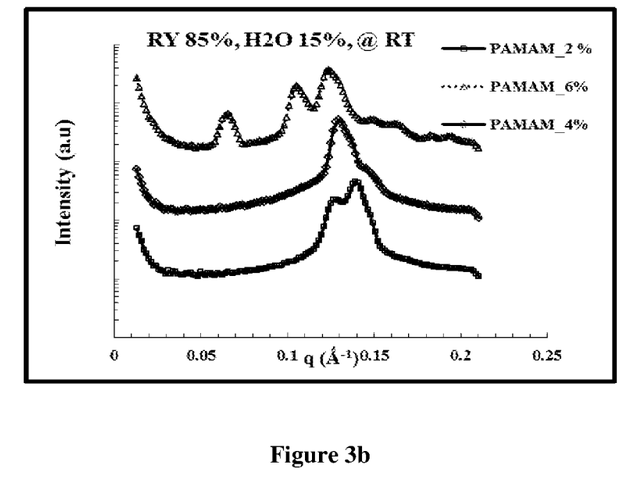
Figure 3C:
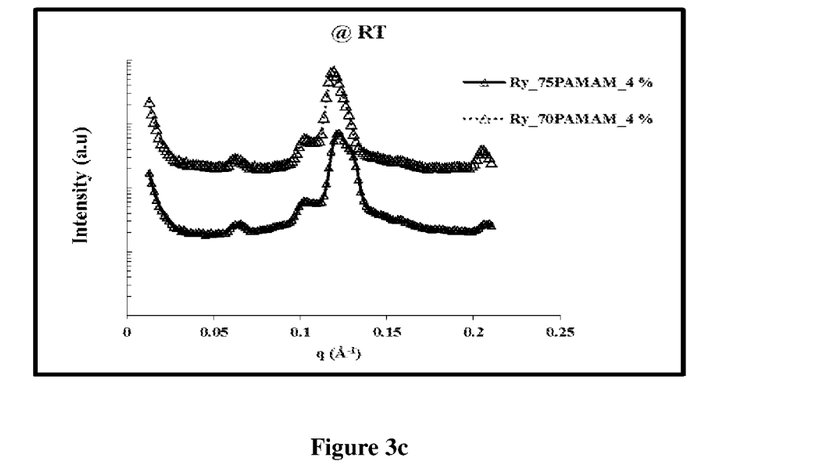

The influence of addition of dendron (i.e PAMAM G2, G3 and G4) at varying loading concentrations on GMO/water system with variation in water content was evaluated (FIG. 3).

For 2% loading of G2 or G3, there was a transition to an $H_{II}$ phase. At higher dendron concentrations (4% and 6 wt %), a transition to the Fd3m phase was observed. This progression through the $H_{II}$ phase, to the Fd3m was also observed at GMO/water ratios of 85/15 and 75/25. $H_{II}$ or coexisting $H_{II}$/Ia3d phases were also observed for GMO/water with 2% G4. Thus, at intermediate dendron concentrations, an $H_{II}$ phase was observed as GMO/water systems transition to the Fd3m phase.

The lattice parameter of GMO/water/dendron system of the present invention was characterized by the cubic Fd3m phase which was always approximately $2\sqrt{2}$ times the $H_{II}$ phase lattice parameter.

Addition of 4 to 6 wt % of PAMAM G4 dendron to GMO/water system, with 15 to 25 wt % water induced Fd3m phase.

The phases were identified using SAXS peak positions: for the Ia3d phase, peaks at q values in the ratio of $\sqrt{6}$, $\sqrt{8}$, $\sqrt{14}$, are observed; at $\sqrt{2}$, $\sqrt{3}$, $\sqrt{4}$, $\sqrt{6}$, for Pn3m and $\sqrt{3}$, $\sqrt{8}$, $\sqrt{11}$, $\sqrt{12}$, for Fd3m. Samples were characterized after several days of equilibration at room temperature, when no further structural change was observed.

Figure 4:
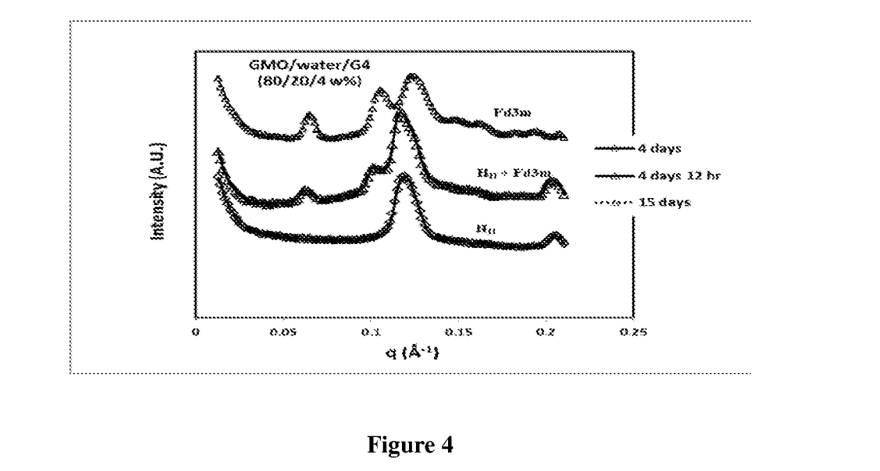
FIG. 4 depicts Kinetics of phase transformation: structural changes for the (80:20:4) GMO/water/G4 systems are observed as a function of equilibration time. This system forms the HII phase in 4 days. Coexistence of the HII and Fd3m phases was observed after about 4.5 days and finally, the Fd3m phase is observed after 15 days of equilibration.
Figure 5A:
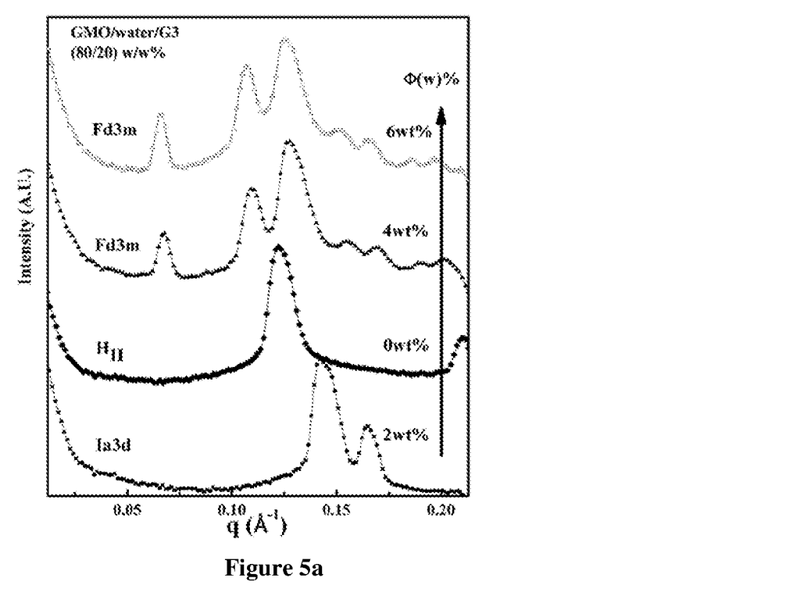
Figure 5B:
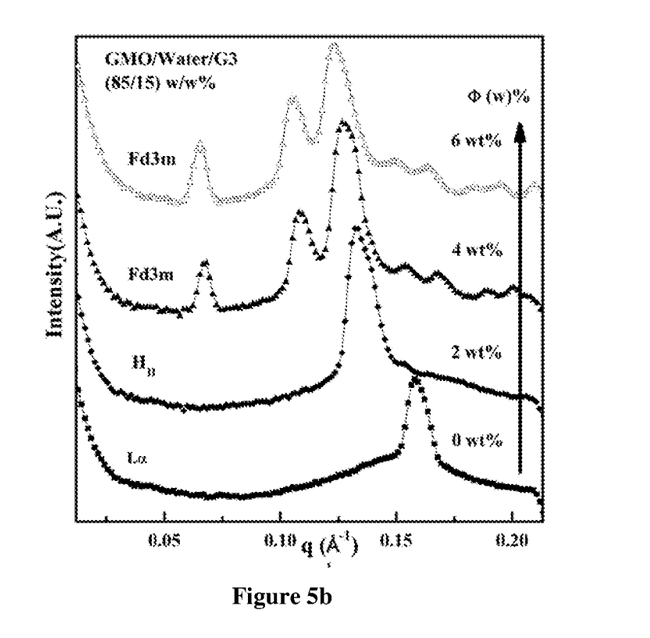
Figure 5C:
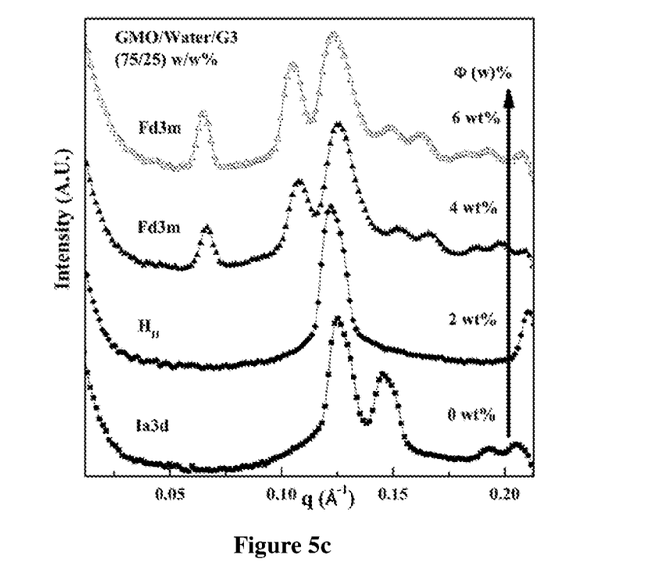

Discontinuous reverse micellar Fd3m phase was formed when second (G2) and third (G3) generation dendrons were added to the 80/20 GMO/water system. The Fd3m phase formation was relatively rapidly for G2 and G3 (~10 days) relative to the G4 (~15 days) dendrons (FIG. 4).

The present invention discloses stable, discontinuous reverse micellar composition stacked in to Fd3m phase comprising polar, compact negatively charged Polysilsesquioxane hydrate-octakistetramethylammonium substituted (POSS) cage of size less than 5 nm, phytantriol and water wherein the weight fraction of POSS relative to GMO and water is 4-10%, the weight fraction of water relative to GMO is 10-40%.

Figure 6:
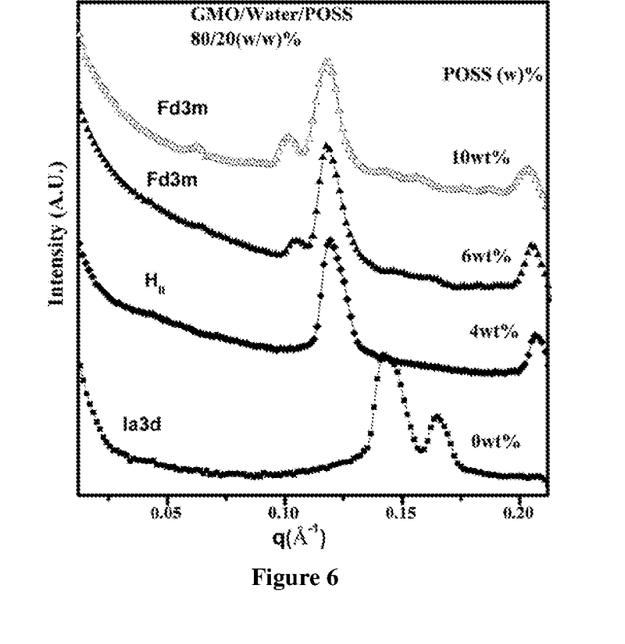
FIG. 6 depicts SAXS data for GMO/water (80/20) containing POSS. Φ represents the amount of POSS in monoolein/water.

In an aspect, for POSS/phytantriol/water phase, a transformation of an 80/20 monoolein water system from a bicontinuous Ia3d structure to an $H_{II}$ phase (for POSS inclusion at weight percent of 2 and 4%) and to an Fd3m phase (at weight percent of 6 and 10%) was observed (FIG. 6).

The present invention relates to a process for preparation of discontinuous reverse micellar composition stacked in Fd3m phase comprising;
a. Mixing 0.5-10 wt % water soluble polar branched polymer of molecular weight 0.5-5 kDa or polar interacting particles of size less than 5 nm or molecular cages of size less than 5 nm to a solution of lipid and water followed by addition of 30% (v/v) $HNO_3$ to adjust pH of the polymer in solution to pH 10;

b. Heating the mixture to a temperature in the range of 60–80° C. and allowing the mixture to equilibrate for a period of 10-15 days to obtain said ternary Fd3m phase.

As herein described in the above process, said polar interacting particles means particles that have a strong attractive interaction with the lipid headgroup.

The water soluble polar branched polymer is selected from acrylics including such as acrylic acid, acrylamide, and maleic anhydride polymers and copolymers; amine-functional polymers including allylamine, ethyleneimine, oxazoline, and other polymers containing amine groups in their main- or side-chain such as polyethyleneimine (PEI), hydroxyalkylacrylate, a hydroxyalkylmethacrylate, a polyhydroxyalkylacrylate, polyhydroxymethacrylate; polyamidoamine; Poly(amino ethyl meth acrylamide and such like.

Preferably, the polymer is selected from branched polymer that bears primary, secondary and tertiary amine groups such as polyethyleneimine (PEI), dendrons that display terminal amine groups selected from polyamidoamine (PAMAM) such as PAMAM G2 amine (with 4-NH2 groups); PAMAM G3 amine (with 8-NH2 groups); PAMAM G4 amine (with 32-NH2 groups).

The particles of size less than 5 nm or molecular cages of size less than 5 nm is selected from Polysilsesquioxane hydrate-octakistetramethylammonium substituted (POSS).

The lipids are selected from ionic or non-ionic surfactants, preferably non-ionic surfactants lipids comprising Glyceryl monooleate (GMO, 2,3-dihydroxypropyloleate), phytantriol (PT, 3,7,11,15-tetramethyl-1,2,3-hexadecanetriol), and other lipids such as monolinolein, monoelaidin, phosphatidylethanolamine, oleoylethanolamide, phospholipids, PEGylated phospholipids, alkyl glycerates, and glycolipids either alone or combination thereof; preferably the non-ionic surfactant is Glyceryl monooleate (GMO, 2,3-dihydroxypropyloleate).

The hydrophilic phase in the composition is water. The weight fraction of water relative to lipid is in the range of 10-40%.

The polymer stock solution comprising of PEI and Dendron were used to prepare the different solution concentrations (0.5 wt. %, 1 wt %, 2 wt. % &4 wt. %) in water. The samples were prepared such that the ratio between the lipid and water was constant for different polymer concentrations. Teflon sealed samples (to avoid the evaporation during heating) were stored at room temperature and measurements were performed after at least 15 days of equilibration. The pharmaceutical composition may further comprise pharmaceutically acceptable excipients known in the art.

The pharmaceutical drug or biologically active component is selected from pharmaceutical drug orbiologically active component with a wide range of molecular weights and water solubility that are used for sustained release in a cubic phase comprising Naproxen sodium, aspirin, vitamin E, propantheline bromide, oxybutynin hydrochloride, metronidazole, tetracycline, timolol maleate, chlorpheniramine maleate, propranolol hydrochloride, melatonin, pindolol, propranolol and pyrimethamine, hemoglobin, cefazolin, insulin, capsaicin, cinnarizine, diclofenac salts, and such like.

The pharmaceutical composition can be in the form of solid, liquid, gel, ointment and such like.

The present invention relates to the process for loading of the drug into the ternary phase system comprising of GMO-water-polymer for controlled/sustained release.

Accordingly, the process for preparing a controlled/sustained release composition comprises forming a mixture of hydrophilic branched polymeric material with MW in the range of 0.5-5 kDa or polar interacting particles of size less than 5 nm or molecular cages of size less than 5 nm in an amount of 0.5% to 10 wt % relative to the lipid/water mixture followed by adding the active to said mixture.

The present invention relates to a method for sustained release of an active selected from pharmaceutical drug or biologically active component, comprising administering to a subject in need thereof an effective amount of pharmaceutical composition comprising discontinuous reverse micelles stacked in a cubic Fd3m phase.

The composition which induces Fd3m phase comprising of polymer-water-GMO system of the present invention is useful in controlled/sustained release of the pharmaceutical drug or biologically active component.

Figure 7:
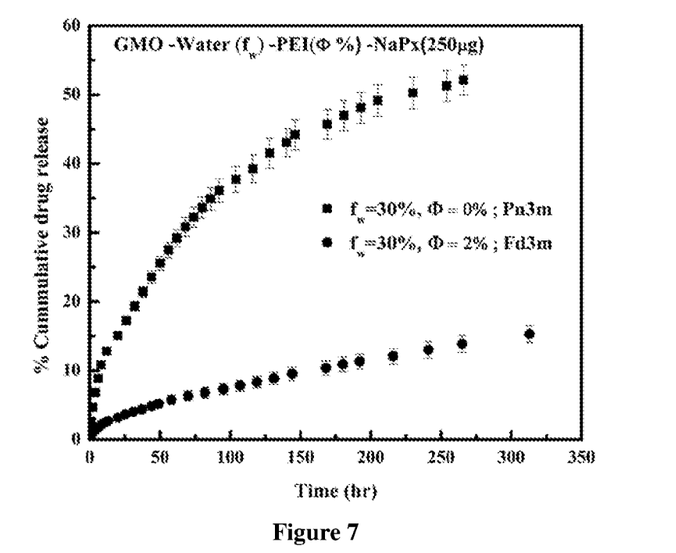
FIG. 7 depicts the release profile of naproxen sodium encapsulated in GMO/water/PEI 2 kDa system

The present invention provides a comparative release profile of the drug, Naproxen sodium loaded in to a bicontinuous phase and in the discontinuous reverse micellar Fd3m phase. About 8.5-fold retardation of the diffusion coefficient was observed in the Fd3m phase compared to the bicontinuous phase (FIG. 7).

Further details of the present invention will be apparent from the examples presented below.

EXAMPLES

Following examples are given by way of illustration and therefore should not be construed to limit the scope of the present invention

Example 1

Preparation of GMO-Water-PEI Ternary Phase 1 g of the Fd3m phase was prepared by mixing 20 mg of 2 wt % PEI to a solution of 784 mg GMO and 196 mg water in the ratio 80:20 (w/w %), followed by addition of 30% (v/v) HNO3 to adjust the pH of the polymer in solution to pH=10. This mixture was heated at 80° C. and then thoroughly mixed. The mixture was allowed to equilibrate for a minimum of 10-15 days to obtain a ternary phase of PEI-water—GMO inducing Fd3m phase.

Example 2

Effect of Hydrophilic Polymer on the Organization of Fd3m Phase

On addition of PEI, the GMO/water sample showed a marked change in appearance and viscosity. In the 90/10% (w/w) GMO/water system that is a low viscosity clear phase in the neat system, addition of 2 wt. % PEI (relative to the GMO/water system) transforms it to a transparent high viscosity gel phase. Further increased PEI content (≥4 wt. %) results in the development of opacity. Similar behavior was observed in the 85/15% (w/w) (GMO/water) system where samples gelled and turned opaque at ≥2 wt % PEI (relative to GMO/water). For all the other GMO/water system (80/20, 75/25, 70/30, 65/35 and 60/40% w/w) the samples turned opaque for PEI >2 wt %.

The phases formed were determined with the help of SAXS. A lamellar phase with 0% PEI (GMO/water: 90/10 & 85/15 w/w) showed a transition into Ia3d phase with 0.3% PEI. For 0.5 wt % PEI, the lamellar phase transformed into the inverse hexagonal phase (H2). When the PEI content exceeded 3%, the GMO/water (90/10) system transformed into the opaque Fd3m phase. Similar behavior was observed with the PEI in the 85/15 (GMO/water) system—however, here the Fd3m phase was formed for ≥2 wt. % PEI.

Example 3

Effect of Temperature and Hydrophilic Polymer on the Phase Diagram of the GMO/Water/PEI System The temperature was varied from ambient to 92° C. Accordingly, the temperature dependent study on all the GMO/water (90/10, 85/15, 80/20, 75/25, 70/30, 65/25, and 60/40 wt. %) compositions with PEI content=0.5, 1, 2 wt. % was conducted. Similarly, the temperature change for the higher molecular weight systems (25 kDa and 70 kDa) was also performed. Fd3m phase was obtained only for a certain range of branched PEI molecular weight (~1-2 kDa) and not for higher molecular weight (25 and 70 kDa).

Example 4

Release Profile of GMO/Water/PEI System

FIG. 7 depicts the release of naproxen sodium from the bicontinuous Pn3m phase and the discontinuous Fd3m phase. 250 μg naproxen sodium was encapsulated in the Pn3m phase formed in 70/30 GMO/water composition. Fd3m phase formed in the same composition of GMO/water (70/30) with 2 w % of the branched polyethylenimine (PEI) was encapsulated with 250 μg naproxen sodium. The Cumulative drug release profile for the naproxen sodium from Fd3m phase was much slower compared the Pn3m phase. For initial 100 hr the release from the Fd3m phase was just 8% whereas from the Pn3m phase it is 48%.

Example 5

Preparation of GMO-Water-G4 (Dendron)

249.75 mg of GMO/water/G4 (in a ratio of 80 parts GMO to 20 parts water and 6 parts G4 dendron) were mixed together and heated at a temperature of 80° C. to obtain a ternary phase. Similarly, Fd3m phases/forms were prepared by the above process using G2 or G3 dendron.

TABLE 1

| Sr. No. | PAMAM Dendron generation (Gn) | Molecular weight in Dalton | Size of the Dendron Rg (nm) | No. of amine group at periphery | Lattice parameter (Å−1) |
|---|---|---|---|---|---|
| 1. | G2 | 740 | 1.45 | 8 | 159.49 |
| 2. | G3 | 1653 | 1.8 | 16 | 162.33 |
| 3. | G4 | 3480 | 2.25 | 32 | 174.036 |

Example 6

Influence of G4 Dendron (i.e PAMAM) on GMO_Water System.

Figure 1:
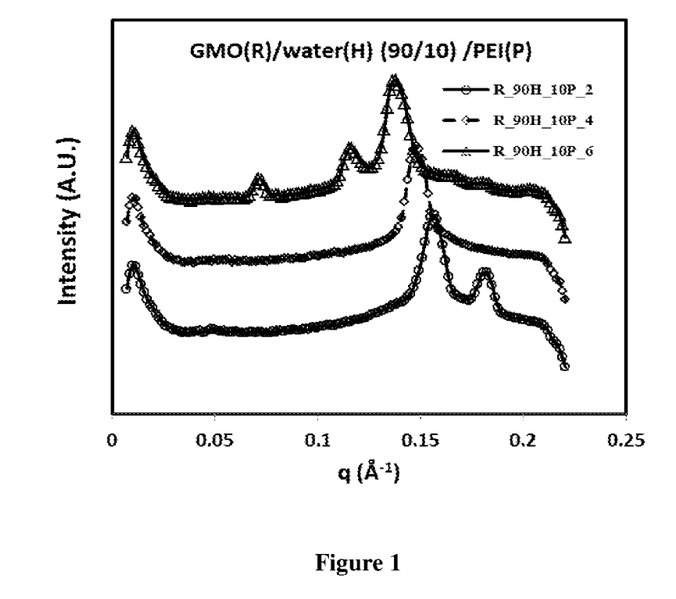
FIG. 1 depicts I (intensity) vs q (peak position) measurement for GMO:water (90%:10%)+PEI % at RT.
Figure 2:
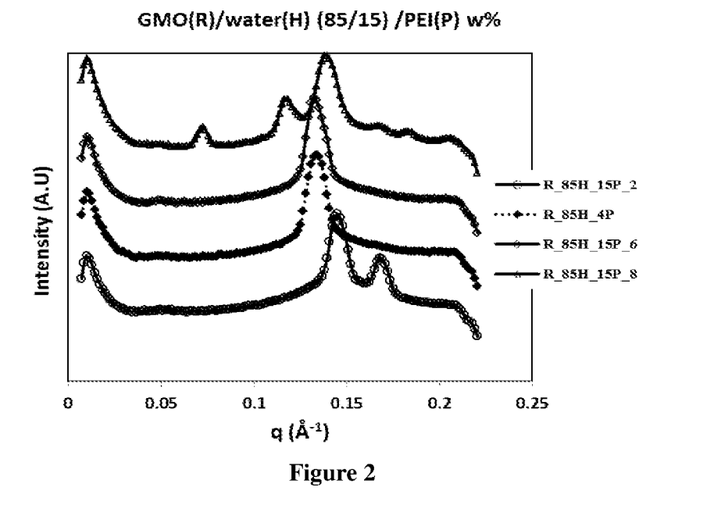
FIG. 2 depicts I (intensity) vs q (peak position) measurement for GMO:water (85%:15%)+PEI % at RT.

PAMAM with ≥4 wt. % induced the transition into the Fd3m phase in GMO/water system while with 2 wt. % H11, and H11+Ia3d coexisting phases are formed. The intensity (I) vs peak position (q) measurements are depicted in FIG. 2 and FIG. 3 respectively.

Example 6

Effect of Poly(Amidoamine) (PAMAM) Dendrons and their Matched Linear Analogs on the Phase Behavior of Monoolein/Water System.

249.75 mg of GMO/water/L4 (in a ratio of 80 parts GMO to 20 parts water and 6 parts L4 linear analog to G4 dendron)

were mixed together and heated at a temperature of 80° C. to obtain a ternary phase. The linear analog was prepared according to procedures reported in H. Wang, J. Zhuang and S. Thayumanavan, ACS Macro Lett., 2013, 2(10), 948-951. The GMO/water/L4 system results in the formation of the continuous Pn3m cubic phase.

Example 7

Loading of Pharmaceutical Drug in GMO/Water/G4 System

Fd3m phase samples was prepared by mixing 249.75 mg of GMO/water/G4 (in a ratio of 80 parts GMO to 20 parts water and 6 parts G4 dendron) with 0.25 mg of Naproxen sodium. The samples were heated to 80° C. and then thoroughly mixed. Subsequently, samples were allowed to equilibrate for several (at least 15) days. Subsequently, release experiments were performed.

Example 8

Preparation of Control (i.e without Polymer)

In control experiments, a bicontinuous cubic phase loaded with Naproxen-Na was prepared by mixing 188.5 mg GMO with 47.1 mg of water and 0.25 mg of Naproxen sodium. Samples were heated to 80° C. and then thoroughly mixed. Subsequently, samples were allowed to equilibrate for several (at least 15) days. Subsequently, release experiments were performed.

Example 9

Release Experiments Protocol:

Sample was taken as a gel at the bottom of a vial and 1.5 ml of distilled water was added carefully on the top of the sample. The water was sampled at 30 minute interval using UV-Vis (absorbance at 232 nm) to measure the solution concentration of the Naproxen. This was used to calculate the total amount of Naproxen released from the sample as a function of time.

Example 10

Figure 8:
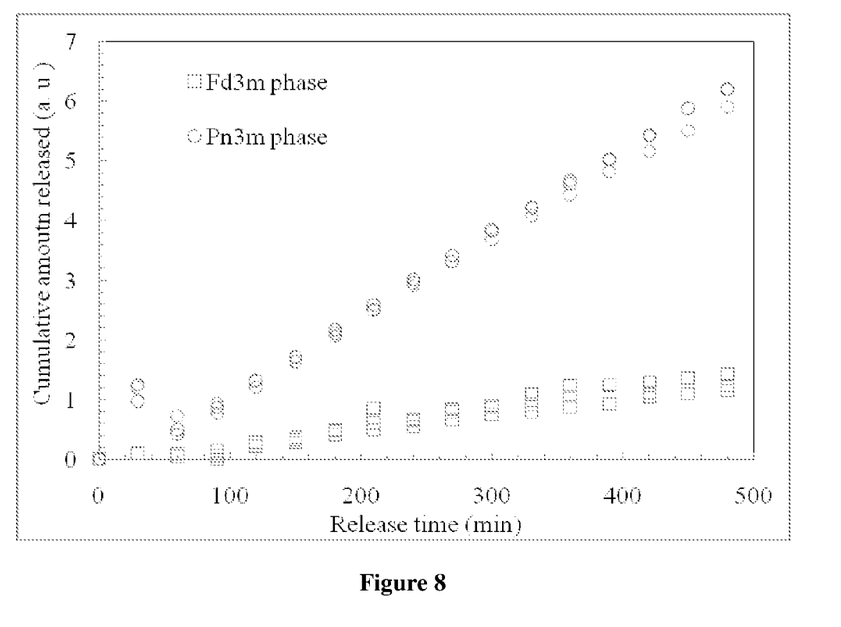
FIG. 8 depicts the comparative release profile of drug, Naproxen Na with Fd3m phase and Pn3m phase.

Release Kinetics Data:

The data compares the release of drug, Naproxen-Na, loaded into a bicontinuous cubic phase (circles) compared with the discontinuous micellar phase (squares). The experiments were repeated three times and all data was plotted to demonstrate reproducibility. This data can be modeled as 1-dimensional diffusion and the diffusion coefficients of drug within the two phases can be modeled. About 8.5-fold retardation of the diffusion coefficient is observed in the Fd3m phase compared to the bicontinuous phase (FIG. 8).

Example 11

Preparation of POSS/Phytantriol/Water System 249.75 mg of Phytantriol/water/POSS (in a ratio of 80 parts GMO to 20 parts water and 6 parts POSS) were mixed together and heated at a temperature of 80° C. to obtain a ternary phase.

Example 12

Effect of Addition of POSS to Phytantriol/Water System

For POSS/phytantriol/water phase, a transformation from a bicontinuous Ia3d structure to an $H_{11}$ phase (for POSS inclusion at weight percent of 2 and 4%) and to an Fd3m phase (at weight percent of 6 and 10%) was observed.

Example 13

Rheological Experiments and X-Ray Scattering Data:

Small angle X-ray scattering (SAXS) experiments were performed on samples to identify their phase. All experiments were carried out on a Bruker Nanostar machine equipped with a Cu rotating anode, with a tungsten filament (filament size 0.1*1 mm) The SAXS was operated at a voltage of 45 kV and current of 20 mA. Characteristic Cu Kα radiation (wavelength=1.54 Å) was used, and calibrated the detector with silver behenate. Samples were sandwiched between kapton films and pasted on a metallic holder with a hole for x-rays to pass through. Scattering data was collected on a multiwire gas filled Hi-star 2-D area detector and were reduced to 1-D using the Bruker offline software.

Rheological experiments were performed to determine the mechanical properties of these mesophases. Experiments were carried on the MCR 301 (Anton Paar) using a 8 mm parallel plate assembly. Samples were carefully loaded on the plate after allowing several days for equilibration. All tests were carried out at 30° C. Initially, a stress ramp was performed to determine the yield stress for the sample. It was then loaded with a fresh sample and creep test at a stress value significantly lower than the yield stress was conducted. The viscosity was calculated from the slope of the compliance curve. The yield stress, creep test parameters and viscosity are shown in Table 2.

TABLE 2

Creep viscosity measurement for GMO/water (80/20) system with G4 and L4 asa function of Ø(wt % of PAMAP)
GMO/Water (80/20)
Composition Stress ramp Stress for creep test Viscosity

| (G4/L4) | Yield stress (τy) Pa | | Pa (τ < τy) | | (η), Pa · s | |
|---|---|---|---|---|---|---|
| Φ (w) % | G4 | L4 | G4 | L4 | G4 | L4 |
| 0 | 2.36 | 2.36 | 0.8 | 0.8 | $10^4$ | $10^4$ |
| 2 | 28.9 | — | 9 | — | $2.5 * 10^4$ | — |
| 4 | 45.6 | 36.3 | 9 | 9 | $2 * 10^5$ | $3.3 * 10^4$ |
| 6 | 68.4 | 11.7 | 9 | 9 | $1.6 * 10^5$ | $1.4 * 10^4$ |

Optical microscopy was performed between crossed polarizers on GMO/water/additive systems, to visualise their textures and identify phases. Nikon Eclipse E600 POL with a conventional digital camera (Nikon) connected to a PC was used. Samples were mounted on a Linkam Shear cell CSS450 for controlled heating. The CSS450 stage was equipped with two heaters for the top and bottom plates. The sample was placed on the lower plate and sandwiched with a glass coverslip. The sample was heated at a rate of 5° C./minute up to ~80° C. and was subsequently cooled to ambient temperature. The $H_{II}$ phase was identified based on characteristic cone type textures and the Lα phase based on their streak-like textures. Polarized optical microscopy was used to assign the SAXS peaks to the $H_{II}$ and Lα phases, since only a few peaks were observed for these phases. Fd3m and Ia3d phases are isotropic, and exhibit no texture under cross polarization.

Advantages of the Invention

1. Induces reverse discontinuous cubic phase (Fd3m phase) using small quantities of hydrophilic polymer with a well-defined size and compact shape, or water dispersable molecular cage of particle.
2. The composition with Fd3m phase provides a delivery system for sustained release of the drug.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

We claim:

1. A stable, discontinuous reverse micellar composition stacked in a cubic Fd3m phase comprising:
   i. a moiety 'A' selected from water soluble branched polymer with molecular weight in the range of 0.5-5 kDa or polar interacting molecular cages of size less than 5 nm, wherein the water soluble branched polymer is selected from polyethyleneimines (PEI) or dendrons of polyamidoamine (PAMAM), and the polar interacting molecular cages is polysilsesquioxane hydrate-octakistetramethylammonium substituted (POSS);
   ii. a moiety 'B' lipids, wherein the moiety 'B' lipids are selected from non-ionic surfactants and the non-ionic surfactant is selected from the group consisting of Glyceryl monooleate (GMO, 2,3-dihydroxypropyloleate), phytantriol (PT, 3,7,11,15-tetramethyl-1,2,3-hexadecanetriol), monolinolein, monoelaidin, phosphatidylethanolamine, oleoylethanolamide, phospholipids, PEGylated phospholipids, alkyl glycerates, and glycolipids and combinations thereof; and
   iii. moiety 'C' a hydrophilic phase;
   wherein weight fraction of moiety 'C' relative to moiety 'B' is in the range of 10-40 wt %; moiety 'A' is in the ratio 0.5-10 wt % relative to moiety 'B' and moiety 'C'.

2. The micellar composition as claimed in claim 1, wherein the dendrons of polyamidoamine (PAMAM) is selected from the group consisting of PAMAM G2 amine with 4-$NH_2$ groups, PAMAM G3 amine with 8-$NH_2$ groups, and PAMAM G4 amine with 32-$NH_2$ groups.

3. The micellar composition as claimed in claim 1, wherein the hydrophilic phase used is water.

4. A pharmaceutical composition comprising of micellar composition as claimed in claim 1 and an active selected from pharmaceutical drug or biologically active component.

5. The pharmaceutical composition as claimed in claim 4, wherein the pharmaceutical drug or biologically active component is selected from the group consisting of Naproxen sodium, aspirin, vitamin E, propantheline bromide, oxybutynin hydrochloride, metronidazole, tetracycline, timolol maleate, chlorpheniramine maleate, propranolol hydrochloride, melatonin, pindolol, propranolol and pyrimethamine, hemoglobin, cefazolin, insulin, capsaicin, cinnarizine, and diclofenac salts.

6. A method for sustained release of an active selected from pharmaceutical drug or biologically active component comprising administering to a subject in need thereof an effective amount of the pharmaceutical composition of claim 4.

7. The micellar composition as claimed in claim 1, wherein the water soluble branched polymer is PEI.

8. The micellar composition as claimed in claim 1, wherein the weight fraction of moiety 'A' is in the ratio of 2-4 wt % relative to moiety 'B' and moiety 'C'.

* * * * *